United States Patent [19]

Rubsamen

[11] Patent Number: 5,364,838
[45] Date of Patent: Nov. 15, 1994

[54] METHOD OF ADMINISTRATION OF INSULIN

[75] Inventor: Reid M. Rubsamen, Berkeley, Calif.

[73] Assignee: Miris Medical Corporation, Hayward, Calif.

[21] Appl. No.: 11,281

[22] Filed: Jan. 29, 1993

[51] Int. Cl.$^5$ .................. A61K 37/26; A61K 37/18; A61K 37/00
[52] U.S. Cl. .................. 514/3; 514/2; 514/4
[58] Field of Search .................. 514/2, 3, 4

[56] References Cited

U.S. PATENT DOCUMENTS 5,011,678 4/1991 Wang et al. .................. 424/45

OTHER PUBLICATIONS

Laube et al, *J. Aerosol Med.*, vol. 4(3) p. 286, 1991.
Wigley et al., *Diabetes*, vol. 20 No. 8, pp. 552–556, 1971
Köhler, *Lung:Suppl*, pp. 677–684, 1990.
Laube et al., *Jama*, vol. 269, No. 16, Apr. 28, 1993, pp. 2106–2109.

*Primary Examiner*—Lester L. Lee
*Assistant Examiner*—A. M. Davenport
*Attorney, Agent, or Firm*—Fish & Richardson

[57] ABSTRACT

A method for treating a patient suffering from diabetes mellitus and a programmed, portable, hand-held device and formulations used in such treatment methodology is disclosed. The programmed device is loaded with a container which includes a formulation comprised of insulin dispersed in a suitable propellant such as a low boiling point propellant. The container may be completely sealed and may be punctured on insertion in the device but preferably includes a single valve which can be opened to release insulin forced from the container by the propellant. A valve for releasing formulation is controlled by an electronic means for opening the valve in response to a measured threshold of airflow which airflow is measured by an airflow detection means positioned between the valve and a mouthpiece. Insulin is administered when the patient inspiratory flow exceeds a preset threshold. The airflow is measured and when a threshold amount of airflow is achieved, the valve opening means is actuated and a controlled amount of insulin is released from the container. The device includes a microprocessor connected to the means for measuring airflow and the means for opening the valve. The microprocessor is programmed to control the amount of insulin released, based on the particular needs of the patient. The device is electronically connectable to a device which measures serum glucose level and can adjust insulin release amounts based of measured glucose levels.

15 Claims, 2 Drawing Sheets

METHOD OF ADMINISTRATION OF INSULIN

FIELD OF THE INVENTION

This invention relates generally to methods of treating humans suffering from diabetes mellitus. More specifically, this invention relates to the controlled intrapulmonary delivery of insulin alone or in combination with other treatment methodologies which are combined to significantly reduce or eliminate the need for administering insulin by injection.

BACKGROUND OF THE INVENTION

Diabetes Mellitus is a disease affecting approximately 7.5 million persons in the United States. The underlying cause of this disease is diminished or absent insulin production by the Islets of Langerhans in the pancreas. Of the 7.5 million diagnosed diabetics in the United States, approximately one-third are treated using insulin replacement therapy. Those patients receiving insulin typically self-administer one or more doses of the drug per day by subcutaneous injection.

Insulin is a peptide hormone with a nominal molecular weight of 6,000 Daltons. Insulin has traditionally been produced by processing pig and cow pancreas to allow isolation of the natural product. More recently, recombinant technology has made it possible to produce human insulin in vitro. It is the currently common practice in the United States to institute the use of recombinant human insulin in all of those patients beginning insulin therapy.

It is known that most proteins are rapidly degraded in the acidic environment of the GI tract. Since insulin is a protein which is readily degraded in the GI tract, those in need of the administration of insulin administer the drug by subcutaneous injection (SC). No satisfactory method of orally administering insulin has been developed. The lack of such an oral delivery formulation for insulin creates a problem in that the administration of drugs by injection can be both psychologically and physically painful.

In an effort to provide for a non-invasive means for administering insulin, and thereby eliminate the need for hypodermic syringes, aerosolized insulin formulations have been theorized. Aerosolized insulin formulations have been shown to produce insulin blood levels in man when these aerosols are introduced onto nasal or pulmonary membrane. Moses et al. [*Diabetes,* Vol. 32, November 1983] demonstrated that a hypoglycemic response could be produced following nasal administration of 0.5 units/kg. Significant inter-subject variability was noted, and the nasal insulin formulation included unconjugated bile salts to promote nasal membrane penetration of the drug. Salzman et al. [*New England Journal of Medicine,* Vol. 312, No. 17] demonstrated that an intranasal aerosolized insulin formulation containing a non-ionic detergent membrane penetration enhancer was effective in producing a hypoglycemic response in diabetic volunteers. Their work demonstrated that nasal irritation was present in varying degrees among the patients studied. In that diabetes is a chronic disease which must be continuously treated by the administration of insulin and in that mucosal irritation tends to increase with repeated exposures to the membrane penetration enhancers, efforts at developing a non-invasive means of administering insulin via nasal administration have not been commercialized.

In 1971, Wigley et al. [*Diabetes,* Vol 20, No. 8] demonstrated that a hypoglycemic response could be observed in patients inhaling an aqueous formulation of insulin into the lung. Radio-immuno assay techniques demonstrated that approximately 10 percent of the inhaled insulin was recovered in the blood of the subjects. Because the surface area of membranes available to absorb insulin is much greater in the lung than in the nose, no membrane penetration enhancers are required for delivery of insulin to the lungs by inhalation. The inefficiency of delivery seen by Wigley was greatly improved in 1979 by Yoshida et al. [*Journal of Pharmaceutical Sciences,* Vol. 68, No. 5] who showed that almost 40 percent of insulin delivered directly into the trachea of rabbits was absorbed into the bloodstream via the respiratory tract. Both Wigley and Yoshida showed that insulin delivered by inhalation could be seen in the bloodstream for two or more hours following inhalation.

Aerosolized insulin therefore can be effectively given if the aerosol is appropriately delivered into the lung. In a review article, Dieter Kohler [*Lung,* supplement pp. 677–684] remarked in 1990 that multiple studies have shown that aerosolized insulin can be delivered into the lung with an expected half-life of 15–25 minutes. However, he comments that "the poor reproducibility of the inhaled dose [of insulin] was always the reason for terminating these experiments." This is an important point in that the lack of precise reproducibility with respect to the administration of insulin is critical. The problems associated with the insufficient administration of insulin cannot be compensated for by administering excess amounts of the drug in that the administration of too much insulin can be fatal.

Effective use of an appropriate nebulizer can achieve high efficiency in delivering insulin to human subjects. Laube et al. [*Journal of Aerosol Medicine,* Vol. 4, No. 3, 1991] have shown that aerosolized insulin delivered from a jet nebulizer with a mass median aerodynamic diameter of 1.12 microns, inhaled via a holding chamber at a slow inspiratory flow rate of 17 liters/minute, produced an effective hypoglycemic response in test subjects at a dose of 0.2 units/kg. Colthorpe et al. [*Pharmaceutical Research,* Vol. 9, No. 6, 1992] have shown that aerosolized insulin given peripherally into the lung of rabbits produces a bioavailability of over 50.7 percent in contrast to 5.6 percent bioavailability seen for liquid insulin dripped onto the central airways. Colthorpe's work supports the contention that aerosolized insulin must be delivered peripherally into the lung for maximum efficiency and that inadvertent central deposition of inhaled aerosolized insulin will produce an effect ten times lower than that desired. Variations in dosing of 10-fold are clearly unacceptable with respect to the administration of most drugs, and in particular, with respect to the administration of insulin.

The present invention endeavors to overcome the problems of the prior art by eliminating the need for permeation enhancers and thus eliminating mucosal irritation and providing a non-invasive methodology for repeatedly providing a controlled dosage amount of insulin to a patient.

SUMMARY OF THE INVENTION

A method for treating a patient suffering from diabetes mellitus and a programmed, portable, hand-held device used in such treatment methodology is disclosed. The programmed device is comprised of a container which includes a formulation comprised of insulin and a suitable propellant which may be a low boiling point propellant and an excipient which facilitates the suspension of insulin in the propellant. The container is completely sealed except for a single valve which can be opened to release insulin forced from the container by the propellant. The valve is controlled by an electronic means for opening the valve in response to any desired signal such as a measured threshold of inspiratory flow measured by an airflow detection means positioned between the valve and a mouthpiece. When the patient withdraws air from the mouthpiece, the patient's inspiratory flow is measured and analyzed. This measurement and analysis makes it possible to analyze the patient's inspiratory flow in terms of liters per minute, as well as the patient's cumulative inspiratory volume, in terms of liters, to be measured. Measurements and analysis are carried out over several inhalations. By analyzing the patient's inspiratory flow created at each inhalation, it is possible to calculate a point or points in the inspiratory cycle which are optimal for the release of insulin to that particular patient. Inspiratory flow data is continuously provided to the microprocessor from the flow transducer in the inspiratory flow path. This information is utilized by the microprocessor which has previously recorded information therein, thus allowing the microprocessor to make a determination to open the valve and release a controlled amount of insulin to the patient. The microprocessor is programmed to take into consideration a variety of characteristics which are particular to the patient or class of patients being treated. Thus, the microprocessor will release the insulin from the container at the most preferred point during the inhalation process of the patient and will deliver a preferred amount in a preferred manner based on the particular needs of the patient, thus providing a highly reproducible means of delivering insulin.

A primary object of the invention is to provide for a non-invasive means of treating diabetes mellitus.

Another object of the invention is to provide a device which allows for the intrapulmonary delivery of controlled amounts of insulin based on the particular needs of the diabetic patient including serum glucose levels and insulin sensitivity.

Yet another object of the invention is to provide a method for the intrapulmonary delivery of insulin which method comprises monitoring a patient's inspiratory flow in terms of rate and volume, calculating a preferred rate and cumulative volume within an inhalation cycle for the release of a drug and automatically releasing drug when the preferred flow rate and cumulative volume have been obtained in a subsequent inhalation cycle based on the patient's inspiratory flow profile.

Another object of the invention is to provide a means for treating diabetes mellitus which involves supplementing insulin administration using an intrapulmonary delivery means in combination with injections of insulin and/or oral hypoglycemic agents such as sulfonylureas.

Another object of the invention is to combine insulin delivery therapies with monitoring technologies so as to maintain tight control over the serum glucose level of a patient suffering from diabetes mellitus.

Yet another object of the invention is to provide methods of treating diabetics using the intrapulmonary delivery of all types of insulin formulations including rapid, intermediate and long-acting preparations.

An advantage of the present invention is that the amount of drug released from the device is controlled by a microprocessor which analyzes data and releases insulin based on an inspiratory flow profile allowing accurate reproducibility of dosing.

Another advantage of the present invention is that the methodology allows the administration of smaller doses of insulin by a convenient and painless route, thus decreasing the probability of insulin overdosing and increasing the probability of safely maintaining desired serum glucose levels.

Another advantage of the present invention is that the device can be readily used in public without the disturbing effects associated with publicly administering a drug by injection.

A feature of the present invention is that the device can be programmed for the particular needs of individual patients.

Another feature of the device of the present invention is that it may be programmed to provide variable dosing so that different doses are delivered to the patient at different times of the day coordinated with meals and/or other factors important to maintain proper serum glucose levels with the particular patient.

Another feature of the invention is that the portable, hand-held inhalation device of the invention can be used in combination with a portable device for measuring serum glucose levels in order to closely monitor and titrate dosing based on actual glucose levels.

Yet another feature of the invention is that the microprocessor of the delivery device can be programmed to prevent overdosing by preventing the valve from being opened more than a given number of times within a given period of time.

These and other objects, advantages and features of the present invention will become apparent to those persons skilled in the art upon reading the details of the structure of the device, formulation of compositions and methods of use, as more fully set forth below.

DETAILED DESCRIPTION OF PREFERRED EMBODIMENTS

Before the present method of treating diabetes mellitus and devices and formulations used in connection with such are described, it is to be understood that this invention is not limited to the particular methodology, devices and formulations described, as such methods, devices and formulations may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "and," and "the" include plural referents unless the context clearly dictates otherwise. Thus, for example, reference to "a formulation" includes mixtures of different formulations, reference to "an analog" refers to one or mixtures of insulin analogs, and reference to "the method of treatment" includes reference to equivalent steps and methods known to those skilled in the art, and so forth.

Unless defined otherwise, all technical and scientific terms used herein have the same meaning as commonly understood by one of ordinary skill in the art to which this invention belongs. Although any methods, devices and materials similar or equivalent to those described herein can be used in the practice or testing of the invention, the preferred methods, devices and materials are now described. All publications mentioned herein are incorporated herein by reference for the purpose of describing and disclosing devices, formulations and methodologies which are described in the publication and which might be used in connection with the presently described invention.

Definitions

The term "insulin" shall be interpreted to encompass natural extracted human insulin, recombinantly produced human insulin, insulin extracted from bovine and/or porcine sources, recombinantly produced porcine and bovine insulin and mixtures of any of these insulin products. The term is intended to encompass the polypeptide normally used in the treatment of diabetics in a substantially purified form but encompasses the use of the term in its commercially available pharmaceutical form which includes additional excipients.

The term "insulin analog" is intended to encompass any form of "insulin" as defined above wherein one or more of the amino acids within the polypeptide chain has been replaced with an alternative amino acid and/or wherein one or more of the amino acids has been deleted or wherein one or more additional amino acids has been added to the polypeptide chain. In general, the "insulin analogs" of the present invention include "super insulin analogs" wherein the ability of the insulin analog to affect serum glucose levels is substantially enhanced as compared with conventional insulin as well as hepatoselective insulin analogs which are more active in the liver than in adipose tissue.

The term "acceptable serum glucose level" is intended to mean a glucose level above 50 mg/dl and below 300 mg/dl more preferably 80 mg/dl to 200 mg/dl and most preferably about 100 mg/dl. It will be understood by those skilled in the art that levels of about 50 mg/dl are considered low and that levels of about 300 mg/dl are considered high, although acceptable in the sense that these levels are generally not fatal. It is an important aspect of the invention to maintain more acceptable levels which are above the low of 50 mg/dl and below the high of 300 mg/dl with it being more acceptable to deliver doses of insulin so as to keep the patient as close as possible to about 100 mg/dl.

The term "dosing event" shall be interpreted to mean the administration of insulin and/or an insulin analog to a patient in need thereof by the intrapulmonary route of administration which event may encompass one or more releases of insulin formulation from an insulin dispensing device over a period of time of 15 minutes or less, preferably 10 minutes or less, and more preferably 5 minutes or less, during which period multiple inhalations are made by the patient and multiple doses of insulin are released and inhaled. A dosing event shall involve the administration of insulin to the patient in an amount of about 1 unit to about 30 units in a single dosing event which may involve the release of from about 10 to about 300 units of insulin from the device.

The term "monitoring event" shall be interpreted to mean an event taking place prior to a "dosing event" whereby the inspiratory flow of the patient's inhalation is measured in order to determine an optimal cumulative volume and inspiratory flow at which to automatically trigger the release of a valve so that insulin can be delivered to the patient. It is preferable to carry out a "monitoring event" prior to each "dosing event" so as to optimize the ability to repeatedly deliver the same amount of insulin to the patient at each dosing event.

The term "inspiratory flow" shall be interpreted to mean a value of airflow calculated based on the speed of the air passing a given point along with the volume of the air passing that point with the volume calculation being based on integration of the flow rate data and assuming atmospheric pressure and temperature in the range of about 18° C. to about 30° C.

The term "inspiratory flow profile" shall be interpreted to mean data calculated in one or more monitoring events measuring inspiratory flow and cumulative volume which profile can be used to determine a point within a patient's respiratory cycle which is optimal for the release of insulin to the patient. It is emphasized that the optimal point within the respiratory cycle for the release of insulin is not calculated based on a point within the cycle likely to result in the maximum delivery of insulin but rather the point in the cycle most likely to result in the delivery of the same amount of insulin to the patient at each release of insulin from the device.

General Methodology

The essence of the invention is to provide a non-invasive means of treating diabetes mellitus in a manner which makes it possible to maintain tight control over serum glucose levels of a patient suffering from the disease. An essential feature of the invention is the intrapulmonary delivery of insulin to the patient in a controlled and repeatable manner. The device of the invention provides a number of features which make it possible to achieve the controlled and repeatable dosing procedure required for treating diabetes. Specifically, the device is not directly actuated by the patient in the sense that no button is pushed nor valve released by the patient applying physical pressure. On the contrary, the device of the invention provides that the valve releasing insulin is opened automatically upon receipt of a signal from a microprocessor programmed to send a signal when data is received from a monitoring device such as an airflow rate monitoring device. A patient using the device withdraws air from a mouthpiece and the inspiratory rate of the patient is measured and cumulative respiratory volume is calculated one or more times in a monitoring event which determines an optimal point in an inhalation cycle for the release of a dose of insulin. Inspiratory flow is measured and recorded in one or more monitoring events for a given patient in order to develop an inspiratory flow profile for the patient. The recorded information is analyzed by the microprocessor in order to deduce a preferred point within the patient's respiratory cycle for the release of insulin with the preferred point being calculated based on the most likely point to result in a reproducible delivery event. The monitoring device continually sends information to the microprocessor, and when the microprocessor determines that the optimal point in the respiratory cycle is reached, the microprocessor actuates the opening of the valve allowing release of insulin. Accordingly, drug is always delivered at a pre-programmed place in the respiratory flow profile of the particular patient which is selected specifically to maximize reproducibility of drug delivery and peripheral dispersion of the drug. It is pointed out that the device of the present invention can be used to, and actually does, improve the efficiency of drug delivery. However, this is not the critical feature. The critical feature is the reproducibility of the release of a tightly controlled amount of drug at a particular point in the inspiratory cycle so as to assure the delivery of a controlled and repeatable amount of drug to the lungs of each individual patient.

The combination of automatic control of the valve release, combined with frequent monitoring events in order to calculate the optimal flow rate and time for the release of insulin, combine to provide a repeatable means of delivering insulin to a patient. Because the valve is released automatically and not manually, it can be predictably and repeatedly opened for the same amount of time each time or for the preprogrammed measured amount of time which is desired at that particular dosing event. Because dosing events are preferably preceded by monitoring events, the amount of insulin released and/or the point in the inspiratory cycle of the release can be readjusted based on the particular condition of the patient. For example, if the patient's total volume should change, such will be taken into account in the monitoring event by the microprocessor which will readjust the amount and/or point of release of the insulin in a manner calculated to provide for the administration of the same amount of insulin to the patient at each dosing event.

It has been found that the ability to tightly control the amount of a volatile propellant formulation of drug delivered via the intrapulmonary route can be improved by delivering smaller doses of the propellant/drug formulation with each release of the valve and with each dosing event. Repeatability, in terms of the amount of insulin delivered to a patient, is improved when the insulin is delivered during a smooth, normal inhalation by the patient. To a certain extent, the ability to provide for a smooth inhalation is enhanced when smaller amounts of insulin are released as compared with larger amounts of insulin. Accordingly, an important aspect of the invention is to deliver aerosolized insulin to a patient in a series of interrupted bursts while the patient continues a single inhaled breath, with ,Bach burst being delivered while the patient maintains optimal inspiratory flow.

Short bursts of the release of insulin can be obtained as two or more bursts but are preferably three or four bursts. The amount of time the valve is opened is generally in the range of about 0.5 seconds to 1 second but is more preferably 0.1 seconds to 0.25 seconds. When the insulin is being released in a series of short bursts, it is preferable for the valve to be open a substantially shorter period of time than the valve is closed. For example, the valve might be opened for approximately 0.1 seconds and closed for approximately 0.5 seconds, followed by another opening of 0.1 seconds and another closing of 0.5 seconds, with this pattern being repeated a plurality of times. Repeatability and dosing can be improved by providing for four bursts, wherein each burst allows for the valve to be opened four times, separated by three closings, wherein the amount of closed time is two to eight times longer than the amount of open time for each on/off event. Particularly preferred repeatability can be obtained by allowing for four bursts, wherein the valve is opened for approximately 0.015 seconds, followed by a closing for approximately 0.1 second, which pattern is repeated for four openings, separated by three closings.

There is considerable variability with respect to the amount of insulin which is delivered to a patient when the insulin is being administered by injection. Patients requiring the administration of injectable insulin use commercial insulin which is prepared in concentrations of 100 units per milliliter, although higher concentrations up to about 500 units per milliliter can be obtained. It is preferable to use the more highly concentrated insulin in connection with the present invention. If insulin containing 500 units of insulin per milliliter is used and a patient is administering 5 units, then the patient will only need to administer 0.01 milliliters of the concentrated insulin to the lungs of the patient to achieve the desired dose.

The symptoms of diabetes can be readily controlled with the administration of insulin. However, it is extremely difficult, and probably impossible, to normalize the blood sugar throughout a 24-hour period utilizing traditional insulin therapy given as one or two injections per day. It is possible to more closely approach normalized blood sugar levels with the present invention. Improvements are obtained by smaller, more frequent dosing and by timing dosing relative to meals, exercise and sleep.

The precise amount of insulin administered to a patient varies considerably depending upon the degree of the disease and the size of the patient. A normal-weight adult may be started on about a 15–20 units a day in that the estimated daily insulin production rate in non-diabetic subjects of normal size is approximately 25 units per day. It is preferable to administer approximately the same quantity of insulin for several days before changing the dosing regime except with hypoglycemic patients for which the dose should be immediately decreased unless a clearly evident nonrecurrent cause of hypoglycemia (such as not eating, i.e., missing a typical meal) is present. In general, the changes should not be more than five to ten units per day. It is typical to administer about two-thirds of the total insulin daily dosage before breakfast and administer the remainder before supper. When the total dosage reaches 50 or 60 units per day, a plurality of smaller doses are often required since peak action of insulin appears to be dose related, i.e., a low dose may exhibit maximal activity earlier and disappear sooner than a large dose. All patients are generally instructed to reduce insulin dosage by about 5 to 10 units per day when extra activity is anticipated. In a similar manner, a small amount of extra insulin may be taken before a meal that contains extra calories or food which is not generally eaten by the diabetic patient. The inhalation device of the present invention is particularly useful with respect to providing such small amounts of additional insulin.

Several types of insulin formulations are commercially available. When larger doses of insulin must be administered at a single point in time, it may be preferable to administer intermediate or long-acting insulin formulations. Such formulations release some insulin immediately and provide a more sustained release of the remainder of the insulin over time. Such formulations are described further below in the "Insulin Containing Formulations" section.

When administering insulin using the inhalation device of the present invention, the entire dosing event can involve the administration of anywhere from one to 25 units, but more preferably involves the administration of approximately five to ten units. The entire dosing event may involve several inhalations by the patient with each of the inhalations being provided with multiple bursts of insulin from the device. For example, the device can be programmed so as to release enough insulin so that approximately one unit of insulin is delivered to the patient per inhalation or 0.33 units of insulin per burst with three bursts being delivered per inhalation. If ten units are to be delivered, the ten units are delivered by releasing 33 bursts in ten different inhalations. Such a dosing event should take about 1–2 minutes to deliver 10 units of insulin. Since only small amounts are delivered with each burst and with each inhalation, even a complete failure to deliver insulin with a given inhalation or burst is not of great significance and will not seriously disturb the reproducibility of the dosing event. Further, since relatively small amounts are delivered with each inhalation and/or burst, the patient can safely administer an additional unit or two of insulin without fear of overdosing.

There is a differential between the amount of insulin actually released from the device and the amount of insulin actually delivered to the patient. In general, the present device is approximately 20% efficient, however, the efficiency can be as low as 10% and as high as 50% meaning that as little as 10% of the released insulin may actually reach the circulatory system of the patient and as much as 50% might be delivered. The efficiency of the delivery will vary somewhat from patient to patient and must be taken into account when programming the device for the release of insulin. In general, a conventional metered dose inhaling device is about 10% efficient.

Obese patients are generally somewhat less sensitive to insulin and must be provided with higher doses of insulin in order to achieve the same effect as normal weight patients. Dosing characteristics based on insulin sensitivity are known to those skilled in the art and are taken into consideration with respect to the administration of injectable insulin. The present invention makes it possible to vary dosing over time if insulin sensitivity changes and/or if user compliance and/or lung efficiency changes over time.

Based on the above, it will be understood that the dosing or amount of insulin actually released from the device can be changed based on the most immediately prior monitoring event wherein the inspiratory flow of a patient's inhalation is measured. The amount of insulin released can also be varied based on factors such as timing and timing is, in general, connected to meal times, sleep times and, to a certain extent, exercise times. Although all or any of these events can be used to change the amount of insulin released from the device and thus the amount of insulin delivered to the patient, ultimately, the amount released and delivered to the patient is based on the patient's serum glucose levels. It is important to maintain the serum glucose levels of the patient within acceptable levels and most preferably to maintain those levels at about 100 mg/dl.

Variations in doses are calculated by monitoring serum glucose levels in response to known amounts of insulin released from the device. If the response in decreasing serum glucose level is higher than with previous readings, then the dosage is decreased. If the response in decreasing serum glucose level is lower than with previous readings, then the dosing amount is increased. The increases and decreases are gradual and are preferably based on averages (of 10 or more readings of glucose levels after 10 or more dosing events) and not a single dosing event and monitoring event with respect to serum glucose levels. The present invention can record dosing events and serum glucose levels over time, calculate averages and deduce preferred changes in administration of insulin.

As another feature of the invention, the device can be programmed so as to prevent the administration of more than a given amount of insulin within a given period of time. For example, if the patient normally requires 25 units per day of insulin, the microprocessor of the inhalation device can be programmed to prevent further release of the valve after 35 units has been administered within a given day. Setting a slightly higher limit would allow for the patient to administer additional insulin, if needed, due to larger than normal meals and/or account for misdelivery of insulin such as due to coughing or sneezing during an attempted delivery.

The ability to prevent overdosing is a characteristic of the device due to the ability of the device to monitor the amount of insulin released and calculate the approximate amount of insulin delivered to the patient based on monitoring given events such as airflow rate and serum glucose levels. The ability of the present device to prevent overdosing is not merely a monitoring system which prevents further manual actuation of a button. As indicated above, the device used in connection with the present invention is not manually actuated, but is fired in response to an electrical signal received from a microprocessor (which received data from a monitoring device such as a device which monitors inspiratory flow) and allows the actuation of the device upon achieving an optimal point in a respiratory cycle. When using the present invention, each release of the valve is a release which will administer drug to the patient in that the valve is released in response to patient inhalation. More specifically, applicant's device does not allow for the release of insulin merely by the manual actuation of a button to fire a burst of insulin into the air.

The microprocessor of applicant's invention can be designed so as to allow for an override feature which would allow for the administration of additional insulin. The override feature could be actuated in an emergency situation. Alternatively, the override feature could be actuated when the device is electronically connected with a serum glucose level monitoring device which determines that serum glucose levels increase to dangerously high levels.

The microprocessor of applicant's invention will also include a timing device. The timing device can be electrically connected with visual display signals as well as audio alarm signals. Using the timing device, the microprocessor can be programmed so as to allow for a visual or audio signal to be sent when the patient would be normally expected to administer insulin. In addition to indicating the time of administration (preferably by audio signal), the device can indicate the amount of insulin which should be administered by providing a visual display. For example, the audio alarm could sound alerting the patient that insulin should be administered. At the same time, the visual display could indicate "five units" as the amount of insulin to be administered. At this point, a monitoring event could take place. After completion of the monitoring event, administration would proceed and the visual display would continually indicate the remaining amount of insulin which should be administered. After the predetermined dose of five units had been administered, the visual display would indicate that the dosing event had ended. If the patient did not complete the dosing event by administering the stated amount of insulin, the patient would be reminded of such by the initiation of another audio signal, followed by a visual display instructing the patient to continue administration.

Additional information regarding dosing with insulin via injection can be found within Harrison's—Principles of Internal Medicine (most recent edition) published by McGraw Hill Book Company, New York, incorporated herein by reference to disclose conventional information regarding dosing insulin via injection.

Supplemental Treatment Methodology

Patients suffering from diabetes mellitus may be treated solely with insulin as indicated above. However, it is possible to treat such patients with a combination of insulin and other drugs such as sulfonylureas which act primarily by stimulating release of insulin from the beta cells in the pancreas. These drugs have the ability of increasing the number of insulin receptors in target tissues and enhance insulin-mediated glucose disposal. Some specific sulfonylurea drugs which can be used in connection with the present invention include acetohexamide administered in an amount of about 500 to 1,500 mg per day; chlorpropamide, administered in an amount of about 50 to 750 mg per day; tolazamide, administered in an amount of about 0.1 to 1 gram per day; tolbutamide, administered in an amount of about 0.5 to 3 grams per day; glipzide administered in an amount of about 2.5 to 40 mg per day and glyburide administered in an amount of about 1.25 to 20 mg per day.

In patients which are producing some insulin, the sulfonylurea drugs may be sufficient to treat the symptoms. Other patients can use a combination of the drugs while administering insulin, while still others require only the administration of insulin. The present invention is beneficial to each type of patient. Further, the present invention allows means for eliminating the need for some patients to take insulin by injection. The patients can be provided with oral doses of sulfonylureas in amounts similar to those indicated above while administering small amounts of insulin via the intrapulmonary route using the device of the present invention. In accordance with one method of the invention, the patient is administered a sulfonylurea drug orally and that treatment is supplemented with insulin administration in relatively small amounts, e.g., five to ten units per dosing event with two to three dosing events per day. Alternatively, the patient is primarily treated by the administration of insulin via the intrapulmonary route and that treatment is supplemented by the oral administration of sulfonylureas of the type described above.

Based on the above, it will be understood by those skilled in the art that a plurality of different treatments and means of administration can be used to treat a single patient. For example, a patient can be simultaneously treated with insulin by injection, insulin via intrapulmonary administration in accordance with the present invention, and sulfonylurea drugs, which are orally administered. Benefits can be obtained by the oral administration of sulfonylurea drugs in that the insulin is naturally released by the patient in a fashion in accordance with real needs related to serum glucose levels. This natural insulin is supplemented by smaller doses provided by intrapulmonary administration in accordance with the present invention. Should such prove to be ineffective for whatever reason, such as breathing difficulties, such could be supplemented by administration via injection.

Treatment via Insulin Analogs

The methodologies of the present invention can be carried out using any type of insulin, although they are preferably carried out using recombinantly produced human insulin. Insulin extracted from animal sources such as bovine or porcine sources can be used. More recently, insulin analogs have been developed. More specifically, novel proteins have been developed wherein the amino acid sequence of the protein is substantially the same as the amino acid sequence of naturally occurring human insulin but for small changes substituting one amino acid for another. These small changes can have important physiological effects with respect to the treatment of diabetes.

There are two general types of insulin analogs presently used. One type of insulin analog is referred to as superactive insulin. In general, superactive insulin has increased activity over natural human insulin. Accordingly, such insulin can be administered in substantially smaller amounts while obtaining substantially the same effect with respect to reducing serum glucose levels. The other general type of analog is referred to as hepatospecific insulin. Hepatospecific insulin analogs are more active in the liver than in adipose tissue and offer several advantages over currently available insulin therapy. Hepatospecific analogs provide preferential hepatic uptake during peripheral subcutaneous administration, thereby mimicking, more closely, the metabolic balance between the liver and the peripheral tissues. Obtaining the correct metabolic balance is an important part of proper treatment of diabetics and administration via the intrapulmonary route should provide advantages over intermuscular injection with respect to obtaining such a balance. It may be desirable to include mixtures of conventional insulin with insulin which is hepatospecific and/or with superactive insulin analogs. Hepatospecific analogs are disclosed and described within published PCT application WO90/12814, published Nov. 1, 1990, which application is incorporated herein by reference for its disclosure of such hepatospecific insulin analogs and in order to disclose other information cited within the other publications referred to within WO90/12814.

U.S. application Ser. No. 074,558 discloses a superactive human insulin analog, [10-Aspattic Acid-B] human insulin, which has increased activity over natural human insulin. Specifically, [10-Aspattic Acid-B] human insulin was determined to be 4 to 5 times more potent than natural insulins. U.S. application Ser. No. 273,957 and International Application Serial No. PCT/US88/02289 disclose other superactive insulin analogs, des-pentapeptide (B26-B30)-[Asp$^{B10}$, Tyr$^{B25}$-α-carboxamide] human insulin, (B26-B30)-[Glu$^{B10}$, Tyr$^{B25}$-α-carboxamide] human insulin, and further insulin analogs of the formula des(B26-B30)-[X$^{B10}$, Tyr$^{B25}$-α-carboxamide] human insulin, in which X is a residue substituted at position 10 of the B chain. These insulin analogs have potencies anywhere from 11 to 20 times that of natural human insulin. All of the above-described insulin analogs involve amino acid substitutions along the A or B chains of natural human insulin, which increase the potency of the compound or change other properties of the compound.

Insulin analogs are not presently used for the treatment of patients on a commercial scale. However, a number of different insulin analogs are being developed and the present invention will be particularly applicable with respect to the delivery of such insulin analogs in that the present invention can be used to provide variable dosing in response to currently measured serum glucose levels. Further, since many insulin analogs are more potent than conventional insulin, their delivery via the intrapulmonary route is particularly convenient.

Monitoring Diabetic Control

All methods of treating diabetes involve measuring glucose levels in some manner. Such measurements are necessary in order to titrate proper dosing and avoid the overadministration of insulin which can result in fatal hypoglycemia. Measurements of urine glucose alone are insufficient to assess diabetic control and bring mean plasma glucose values into a near normal range since the urine will be free of glucose when the plasma concentration is less than 180 mg/dl. For this reason, "home glucose monitoring" is used in those patients treated by continuous subcutaneous insulin infusion (CSII) or multiple subcutaneous injection (MSI) techniques. Such monitoring requires capillary blood which can be obtained in a substantially painless manner using a small spring-triggered device referred to as Autolet™ produced by Ulstr Scientific Incorporated which device is equipped with small disposable lancelets. The amount of glucose is analyzed using chemically impregnated strips which are read in a commercially available reflectance meter. One commercially available strip is referred to as Chemstrip bG (produced by Bio-Dynamics). The Chemstrip bG can provide satisfactory values by visual inspection utilizing a dual-color scale, thus eliminating the need for a reflectance meter. Frequent measurement of the plasma glucose (a fairly standard program utilizes seven or eight assays over a 24-hour period) allows a reasonable assessment of mean plasma glucose levels during the day and guides adjustment of insulin dosage.

The methodology of the present invention is preferably utilized in combination with a closely controlled means of monitoring serum glucose levels. More specifically, the drug delivery device of the invention is used to administer doses of insulin via the intrapulmonary route. The doses may be administered in somewhat smaller amounts than are generally administered by injection. The amount of insulin administered can be readily adjusted in that smaller amounts are generally administered using the intrapulmonary delivery methodology of the present invention. During the day, as insulin is administered, serum glucose levels are frequently monitored. The amount of insulin administered can be dosed based on the monitored serum glucose levels, i.e., as glucose levels increase, the amount of insulin can be increased, and as glucose levels are seen to decrease, the dosing of insulin can be decreased. It will be noted that there is some "lag" time between the administration of a dose of insulin and its effect on serum glucose levels. Accordingly, when glucose levels are seen to increase and insulin is administered, sufficient time should be allowed for the glucose level to decrease prior to the administration of additional insulin in order to avoid overdosing. However, as indicated above, the present device can be readily programmed so as to prevent excessive administration of insulin by programming the microprocessor to not allow the release of the valve if the valve has been released a given number of times within a given period of time. Further, it will be understood that there is generally less "lag" time with intrapulmonary administration as compared to SC injection.

Based on the information disclosed herein in combination with what is known about insulin dosing and serum glucose levels, computer readable programs can be readily developed which can be used in connection with the insulin delivery device of the present invention. More specifically, the microprocessor can be programmed so as to deliver precise doses of insulin which correspond to the particular needs of the patient based on serum glucose monitoring information which is supplied to the microprocessor of the device of the invention. Further, the dosing information contained within the microprocessor of the device of the invention can be fed to a separate computer and/or serum glucose monitoring device (preferably portable) in order to calculate the best treatment and dosing schedule for the particular patient.

Insulin Containing Formulations

A variety of different insulin containing formulations can be used in connection with the present invention. The active ingredient within such formulations is insulin which is preferably recombinantly produced human insulin but, as indicated above, may include insulin extracted from animal sources. Further, the insulin may be an insulin analog which is an analog of human insulin which has been recombinantly produced. Although the insulin and/or analog is generally present by itself as the sole active ingredient, the insulin may be present with an additional active ingredient such as a sulfonylurea. However, such sulfonylureas are generally administered separately in order to more closely control dosing and serum glucose levels.

Regardless of the active ingredient, there are four basic types of insulin formulations which can be used in connection with the present invention. All of the formulations include insulin, preferably with a pharmaceutically acceptable carrier suitable for intrapulmonary administration. In accordance with two preferred formulations, a low boiling point, highly volatile propellant is combined with the active ingredient and a pharmaceutically acceptable excipient. In one of the two formulations, the active ingredient is provided as a suspension or dry powder in the propellant, and in the other formulation, the active ingredient is dissolved in solution within the propellant. Both of these formulations may be readily included within a container which has a valve as its only opening. Since the propellant is highly volatile, i.e., has a low boiling point, the contents of the container will be under pressure. In accordance with another formulation, the insulin is provided as a dry powder by itself, and in accordance with still another formulation, the insulin or active ingredient is provided in a solution formulation.

Any formulation which makes it possible to produce aerosolized forms of insulin which can be inhaled and delivered to a patient via the intrapulmonary route can be used in connection with the present invention. Specific information regarding formulations which can be used in connection with aerosolized delivery devices are described within Remington's Pharmaceutical Sciences, A. R. Gennaro editor (latest edition) Mack Publishing Company. Regarding insulin formulations, it is also useful to note Sciarra et al. [*Journal of Pharmaceutical Sciences,* Vol. 65, No. 4, 1976]. When low boiling point propellants are used, the propellants are held within a pressurized canister of the device and maintained in a liquid state. When the valve is actuated, the propellant is released and forces the active ingredient from the canister along with the propellant. The propellant will "flash" upon exposure to the surrounding atmosphere, i.e., the propellant immediately evaporates. The flashing occurs so rapidly that it is essentially pure active ingredient which is actually delivered to the lungs of the patient. The "flashing" phenomenon which occurs with the use of low boiling point propellants greatly increases the practicality of the present invention as compared with nebulizers or formulations which do not use such propellants in that larger amounts of drug can be easily administered in a short period of time. Further, since the material being delivered to the lungs is essentially pure drug, it is easier to monitor and more closely control dosing which is a critical feature of the methodology of the present invention. Accordingly, it is preferable to use low boiling point propellants such as low boiling point chlorofluorocarbons or hydrocarbons, e.g., trichlorofluormethane and dichlorodifluoromethane. As non-chlorofluorocarbon containing propellants are developed which are low boiling point propellants, their use in connection with the present invention will become apparent to those skilled in the art.

The most preferred formulation of the present invention is a suspension formulation wherein a dry powder of insulin is suspended within a low boiling point propellant with an excipient such as oleic acid. Such low boiling point propellants are referred to by conventional nomenclature and two particularly preferred propellants are "P12" and "P114" with a particularly preferred formulation being a 50-50 combination of P12 and P114. A somewhat less preferred formulation includes the active ingredient being included in a solution such as the type of solution which is made commercially available for injection and/or other solutions which are more acceptable for intrapulmonary delivery. With such formulations, the propellant is pressurized gas. When preparing preferred formulations of the invention which provide for the insulin, excipient and low boiling point propellant, any pharmaceutically acceptable excipient may be used provided the excipient is capable of allowing suspension of the insulin with the propellant. Compounds such as oleic acid and related oils having a carbon chain length in the range of about 12-30 carbons can be used with oleic acid being particularly preferred.

Less preferred formulations include the dry powder by itself. When such a formulation is used, it may be used in combination with a gas propellant which gas propellant is released over a predetermined amount of dried powder which is forced into the air and inhaled by the patient. It is also possible to design the device so that a predetermined amount of dry powder is placed behind a gate. The gate is opened in the same manner as the valve is released when a predetermined airflow rate is obtained. Thereafter, the dry powder is inhaled by the patient and the insulin is delivered. When solution formulations are used, a compressed gas is used to force the solution from the container and create an aerosolized form of the solution which can be inhaled by the patient.

Formulations of the invention can include liposomes containing insulin in combination with an amount of alveolar surfactant protein effective to enhance the transport of the liposomes across the pulmonary surface and into the circulatory system of the patient. Such liposomes and formulations containing such are disclosed within U.S. Pat. No. 5,006,343, issued Apr. 9, 1991, which is incorporated herein by reference to disclose liposomes and formulations of liposomes used in intrapulmonary delivery. The formulations and methodology disclosed in U.S. Pat. No. 5,006,343 can be adapted for the application of insulin and included within the delivery device of the present invention in order to provide for effective treatments of diabetic patients.

The terms "insulin" and "insulin analog" have been defined above. With respect to both terms, applicant points out that a variety of commercial insulin formulations are available. Rapidly acting preparations are always indicated in diabetic emergencies and in CSII and MSI programs. Intermediate preparations are used in conventional and MSI regimens, and long-acting formulations are used rarely. It is not possible to delineate precisely the biologic responses to the various preparations because peak effects and duration vary from patient to patient and depend not only on route of administration but on dose. The various insulins are available as rapid (regular, semilente), intermediate (NPH, lente, globin), and long-acing (PZI, ultralente) preparations, although not all manufacturers offer all varieties. Lente and NPH insulin are used in most conventional therapy and are roughly equivalent in biologic effects, although lente appears to be slightly more immunogenic and to mix less well with regular insulin than does NPH.

Delivery Device

Figure 1:
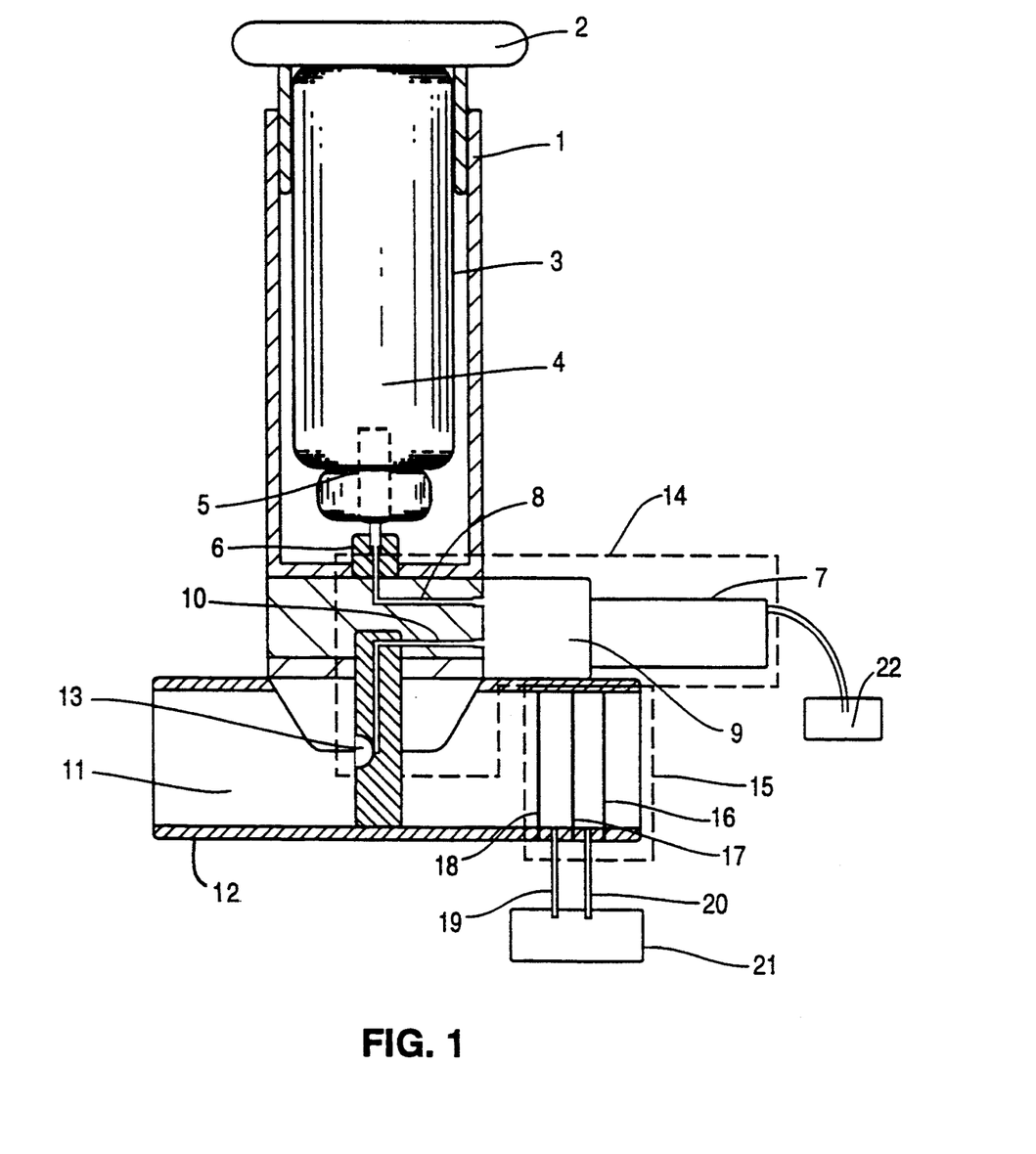
FIG. 1 is a cross-sectional view of an embodiment of an aerosolizing drug delivery device.
Figure 2:
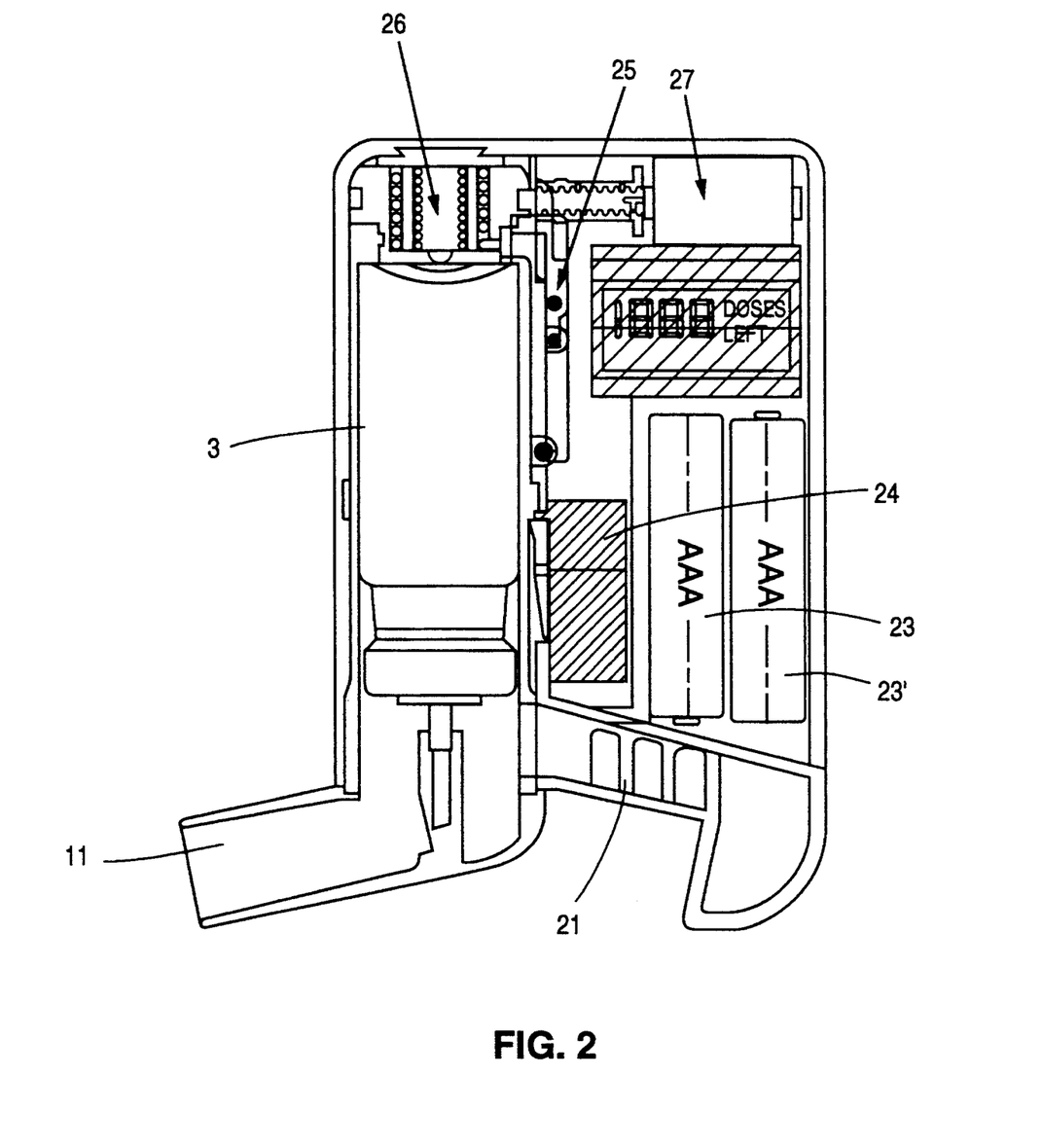
FIG. 2 is another embodiment of an aerosolizing drug delivery device which can be used in the intrapulmonary delivery of insulin in connection with the present invention.

Before referring to the specific embodiments of the delivery device shown in FIGS. 1 and 2, an explanation will be provided regarding a general mechanism which can be used in connection with the method of intrapulmonary administration of insulin. Such a device is a hand held, portable device which is comprised of (a) a means for analyzing the inspiratory flow of a patient and (b) a means for automatically releasing a measured amount of drug into the inspiratory flow path of a patient, e.g. an automatic valve actuation means. In order to use the device, the device must be "loaded", i.e. connected to (c) a source of drug which, in general, is an insulin suspension dispersed within a low boiling point propellant. The entire device is light weight (less than 1 kg loaded) and portable.

A formulation of insulin in a low boiling point propellant is typically contained in a pressurized canister which is connectable to the "unloaded" device, i.e., the device without the container. When the container of propellant and insulin is connected to the device, the container will include a valve opening at one end which opening is seated into a flow path within the device. The device preferably includes a mouth piece at the end of the flow path, and the patient inhales from the mouth piece which causes an inspiratory flow to be measured within the flow path. This inspiratory flow causes an air flow transducer to generate a signal. This signal is conveyed to a microprocessor which is able to convert, continuously, the signal from the transducer in the inspiratory flow path to a flow rate in liters per minute. The microprocessor can further integrate this continuous air flow rate signal into a representation of cumulative inspiratory volume. At an appropriate point in the inspiratory cycle, the microprocessor can send a signal to an actuation means. When the actuation means is signaled, it releases a valve allowing drug and propellant to escape into the inspiratory flow path of the device and ultimately into the patient's lungs. After being released, the drug and propellant will preferably pass through a nozzle prior to entering the inspiratory flow path of the device and thereafter the lungs of the patient.

It is important to note that the firing threshold of the device is not based on a single criterion such as the rate of air flow through the device or a specific time after the patient begins inhalation. The firing threshold is based on an analysis of the patient's inspiratory flow profile. This means that the microprocessor controlling the device takes into consideration the instantaneous air flow rate as well as the cumulative inspiratory flow volume when it determines the optimal point in the patient's inspiratory cycle which would be most preferable in terms of reproducibly delivering the same amount of drug to the patient with each release of drug. Further, the device preferably includes a means for recording a characterization of the inspiratory flow profile for the patient which is only possible by including a microprocessor in combination with a read/write memory means and a flow measurement transducer. By using such devices, it is possible to change the firing threshold at any time in response to an analysis of the patient's inspiratory flow profile, and it is also possible to record drug dosing events over time. FIG. 1 shows a cross-sectional view of a hand held, portable, electronic breath-actuated inhaler device which can be used in connection with the present invention. The device is shown with a holder 1 having cylindrical side walls and a removable cap. The holder 1 is "loaded" in that it includes the pressurized canister 3. The canister 3 includes a non-metering valve 5 which is held down in the open position when the cap 2 is screwed down, thus setting the valve 5 into a seat 6 which is in connection with a flow path 8.

A formulation 4 comprised of insulin and a suitable propellant, such as a low boiling point propellant, is contained within the pressurized canister 3. Propellant and insulin are released from the canister 3 via the electrically controlled solenoid 7. In that the valve 5 of the canister is continuously open, another valve, contained within solenoid 7, facilitates the release of the drug. When the solenoid 7 allows release of propellant and insulin, the propellant and insulin flows through the flow path 8 and then through the solenoid actuated valve 9 into the flow path 10 out through nozzle 13 and then into the inspiratory flow path 11 surrounded by walls 12.

It is important to note that a variety of devices can be used in order to carry out the insulin delivery methodology of the present invention. However, the device must be capable of allowing the release of a metered amount of insulin based on pre-programmed criteria which are readable by the microprocessor 22. The pre-programmed information is contained within a nonvolatile memory which can be modified via an external device. In another embodiment, this pre-programmed information is contained within a "read only" memory which can be unplugged from the device and replaced with another memory unit containing different programming information. In yet another embodiment, microprocessor 22, containing read only memory which in turn contains the pre-programmed information, is plugged into the device. For each of these three embodiments, changing the programming of the memory device readable by microprocessor 22 will radically change the behavior of the device by causing microprocessor 22 to be programmed in a different manner. As regards the present invention, the non-volatile memory contains information relevant only to the administration of insulin. Microprocessor 22 sends signals to solenoid 7 which determines the amount of drug delivered into the inspiratory flow path. Further, microprocessor 22 keeps a record of all drug dosing times and amounts using a read/write non-volatile memory which is in turn readable by an external device. The formulation 4 contained within canister 3 is released into the atmosphere ultimately via nozzle 13 which opens into inspiratory flow path 11. It is at this point that the low boiling point propellant within formulation 4 flashes, i.e. rapidly evaporates, thus providing particles of insulin in an aerosol which is introduced into the mouth and ultimately into the lungs of the patient. In order to allow for ease of use, it is possible to form inspiratory flow path 11 into a mouth piece which can be specifically designed to fit the mouth of a particular patient using the device.

The solenoid 7, and associated valve 9, flow paths 8 and 10, as well as nozzle 13 make up the aerosol delivery system 14 shown by the dotted lines within FIG. 1. The system 14 is in connection with the flow sensor 15 which is capable of measuring a flow rate of about 0 to about 300 liters per minute. The flow sensor 15 includes screens 16, 17 and 18 which are positioned approximately ¼" apart from each other. Tubes 19 and 20 open to the area between the screens 16, 17 and 18 with the tubes 19 and 20 being connected to a conventional differential pressure transducer 21. When the user draws air through inspiratory flow path 11, air is passed through the screens 16, 17 and 18 and the air flow can be measured by the differential air pressure transducer 21. The flow sensor 15 is in connection with the aerosol delivery system 14, and when a threshold value of air flow is reached, the aerosol delivery system 14 allows the release of formulation 4 so that insulin is delivered to the patient. Solenoid 7 is connected to a microprocessor 22 via an electrical connection. The details of the microprocessor and the details of other drug delivery devices which might be used in connection with the present invention are described and disclosed within U.S. patent application Ser. No. 07/664,758, filed on Mar. 5, 1991 entitled "Delivery of Aerosol Medications for Inspiration" which application is incorporated in its entirety herein by reference, and it is specifically incorporated in order to describe and disclose devices as shown within FIG. 1 and the microprocessor and program technology used therewith.

A cross-sectional view of yet another (and more preferred) embodiment of the hand held, electronic, breath-actuated inhaler device of the invention is shown in FIG. 2. The device of FIG. 2 shows all of the components present within the single hand held, portable device, i.e. the power source not shown in FIG. 1 is shown in the device in FIG. 2. Like the device shown within FIG. 1, the device of FIG. 2 includes a canister 3 which includes a canister valve 5. However, unlike the device of FIG. 1, the device of FIG. 2 does not have the valve continuously open but allows a valve 5 connected to the canister 3 to be opened by the mechanical force generated by a valve actuation mechanism 26 which is a motor driven, mechanical mechanism powered by a power source such as batteries 23 and 23'. However, like the device shown within FIG. 1, the patient inhales through inspiratory flow path 11 which can form a mouth piece in order to obtain a metering event using the differential pressure transducer 21. Further, when the inspiratory flow meets a threshold of a pre-programmed criteria, the microprocessor 24 sends a signal to an actuator release mechanism 25 which includes a motor 27 and actuates the actuation mechanism 26 forcing canister 3 downward so that canister valve 5 releases formulation into the inspiratory flow path 11. Further details regarding the device of FIG. 2 are described within co-pending U.S. patent application entitled "An Automatic Aerosol Medication Delivery System and Methods", filed on Jan. 29, 1993 as Ser. No. 08/002,507, which application is incorporated herein by reference in its entirety and specifically incorporated in order to describe and disclose devices as shown within FIG. 2 and the microprocessor and program technology used therewith.

Microprocessor 24 of FIG. 2 includes an external non-volatile read/write memory subsystem, peripheral devices to support this memory system, reset circuit, a clock oscillator, a data acquisition subsystem and an LCD annunciator subsystem. The discrete components are conventional parts which have input and output pins configured in a conventional manner with the connections being made in accordance with instructions provided by the device manufacturers. The microprocessor used in connection with the device of the invention is designed and programmed specifically so as to provide controlled and repeatable amounts of insulin to a patient upon actuation. Adjustments can be made in the program so that when the patient's inspiratory flow profile is changed such is taken into consideration. This can be done by allowing the patient to inhale through the device as a test in order to measure air flow with preferred drug delivery points determined based on the results of several inhalations by each particular patient. This process can be readily repeated when the inspiratory flow profile is changed for whatever reason, e.g. recent exercise congestion. Determination of optimal drug delivery points in the inspiratory flow can be done at each dosing event, daily, weekly, or with the replacement of a new canister in the device.

The microprocessor of the present invention, along with its associated peripheral devices, can be programmed so as to prevent the release of drug from the canister from occurring more than a given number of times within a given period of time. This feature makes it possible to prevent overdosing the patient with insulin. The overdose prevention feature can be particularly designed with each individual patient in mind or designed with particular groups of patients in mind. For example, the microprocessor can be programmed so as to prevent the release of more than approximately 35 units of insulin per day when the patient is normally dosed with approximately 25 units of insulin per day. The systems can also be designed so that only a given amount of insulin is provided at a given dosing event. For example, the system can be designed so that only approximately 10 units of insulin is given in a given 15-minute period over which the patient will make approximately 10 inhalations with one unit of insulin being delivered with each inhalation. By providing this feature, greater assurances are obtained with respect to delivering the insulin gradually over time.

Another feature of the device is that it may be programmed so as to take into account the chronobiology of the patient. More specifically, the program can be designed so that audio signals or visual signals or a combination of audio and visual signals are provided to the patient advising the patient that insulin should be administered. The timing of these signals is set to the particular biology or chronobiology of the patient, taking into account normal serum glucose levels of that patient and/or the particular time of day. When the signal is provided, the patient will administer what is believed to be the appropriate amount of insulin for that particular time of day.

The microprocessor of the invention can be connected to external devices permitting external information to be transferred into the microprocessor of the invention and stored within the non-volatile read/write memory available to the microprocessor. The microprocessor of the invention can then change its drug delivery behavior based on this information transferred from external devices. For example, as indicated above, it is critical to periodically monitor serum glucose levels in a patient suffering from diabetes. The glucose level information can be provided to the microprocessor, recorded in the associated read/write non-volatile memory, and appropriate calculations made in order to determine if additional insulin should be provided or if a decreased amount of insulin should be administered. This feature adds to the convenience of the invention and increases the safety of the entire dosing methodology. Further, this feature makes it possible to interrelate the intrapulmonary delivery of insulin with other treatment methodologies such as the administration of oral hypoglycemic agents and injected insulin. All of the features of the invention are provided in a portable, programmable, battery-powered, hand-held device for patient use which has; a size which compares favorably with existing metered dose inhaler devices.

In addition to monitoring serum glucose levels in order to determine proper insulin dosing, the microprocessor of the present invention is programmed so as to allow for monitoring and recording data from the inspiratory flow monitor without delivering drug. This is done in order to characterize the patient's inspiratory flow profile in a given number of monitoring events, which monitoring events preferably occur prior to dosing events. After carrying out a monitoring event, the preferred point within the inspiratory cycle for drug delivery can be calculated. This calculated point is a function of measured inspiratory flow rate as well as calculated cumulative inspiratory flow volume. This information is stored and used to allow activation of the valve when the inhalation cycle is repeated during the dosing event. The devices of FIGS. 1 and 2 have been put forth in connection with devices which use a low boiling point propellant and preferably use that propellant in combination with a suspension formulation which includes the dry powdered insulin within the low-boiling-point propellant. Those skilled in the art will readily recognize that such devices can be used for administering a solution of insulin within the low-boiling-point propellant. However, those skilled in the art will also readily recognize that different mechanisms will be necessary in order to deliver different formulations, such as a dry powder without any lo propellant. A device could be readily designed so as to provide for the mechanical movement of a predetermined amount of dry powder to a given area. The dry powder would be concealed by a gate, which gate would be opened in the same manner described above, i.e., it would be opened when a predetermined flow rate level and cumulative volume have been achieved based on an earlier monitoring event. Patient inhalation would then cause the dry powder to form a dry dust cloud and be inhaled. Dry powder can also be aerosolized by compressed gas, and a solution can be aerosolized by a compressed gas released in a similar manner and then inhaled.

The instant invention is shown and described herein in which is considered to be the most practical and preferred embodiments. It is recognized, however, that the departures may be made therefrom which are within the scope of the invention and that obvious modifications will occur to one skilled in the art upon reading this disclosure.

I claim:

1. A method of intrapulmonary administration of insulin, comprising:

measuring the inspiratory flow of a patient and calculating a threshold level in an inhalation cycle at which release of drug is to take place, the threshold level being determined in a manner so as to maximize the repeatability of the amount of insulin delivered to the patient on releasing insulin;

releasing a metered dose of aerosolized insulin from a pressurized canister containing insulin in combination with a low boiling point propellant, the releasing being carried out upon reaching the threshold level generated by the patient inhaling;

inhaling the metered dose of aerosolized insulin into the lungs of a patient; and monitoring serum glucose levels within the patient;

wherein the measuring, releasing, inhaling and monitoring steps are continuously repeated in a manner so as to maintain a desired serum glucose level in the patient.

2. The method of claim 1, wherein information obtained from the monitoring is electronically processed by a microprocessor programmed to release insulin in a manner so as to maintain a desired serum glucose level in the patient.

3. The method of claim 1, further comprising:

repeating the measuring prior to each releasing, inhaling and monitoring step over a period of time so as to maintain a desired serum glucose level in the patient.

4. The method of claim 1, wherein the insulin is recombinantly produced human insulin.

5. The method of claim 1, wherein the insulin is extracted from an animal source selected from the group consisting of bovine and porcine.

6. A method of intrapulmonary administration of insulin, comprising:

measuring the inspiratory flow of a patient during an inhalation cycle prior to administering insulin and calculating a threshold level of airflow prior to administering insulin, wherein the threshold level of inspiratory flow is determined in a manner so as to maximize repeatability of the amount of insulin delivered to the patient on releasing insulin;

administering insulin to the patient by the intrapulmonary route, the insulin being administered from a hand-held, self-contained device which releases insulin on detecting the threshold level of inspiratory flow created by patient inhalation;

monitoring serum glucose levels in the patient; and repeating the measuring, administering and monitoring steps a plurality of times over a period of time so as to maintain a desired serum glucose level in the patient.

7. The method as claimed in claim 6, wherein the amount of insulin administered and the glucose level monitored are continually recorded electronically by the self-contained device and adjustments are made in the amount of insulin administered based on the effect of insulin administration on the glucose levels of the patient.

8. The method as claimed in claim 6, wherein the amount of insulin administered is in the range of 1 unit per day to 50 units per day.

9. The method as claimed in claim 6, wherein the desired serum glucose level in the patient is within the range of 50 mg/dl to 300 mg/dl.

10. The method as claimed in claim 6, wherein the insulin is recombinantly produced human insulin.

11. The method as claimed in claim 6, wherein the insulin is insulin extracted from an animal source group consisting of a bovine source and a porcine source.

12. The method of claim 6, further comprising:

orally administering a sulfonylurea drug to the patient.

13. The method of claim 12, wherein the sulfonylurea drug is selected from the group consisting of acetohexamide, chlorpropamide, tolazamide, tolubutamide, glipzide and glyburide.

14. The method of claim 6, wherein the monitoring is carried out prior to each dosing event, wherein insulin is administered to the patient.

15. A method of intrapulmonary administration of insulin, comprising:

placing a mouthpiece of a hand-held, metered dose inhaler device in the mount of a patient, wherein the device is comprised of a container having therein insulin and a low boiling point propellant, a valve for releasing insulin and propellant from the container to the mouthpiece, a means for measuring airflow created by drawing air from the mouthpiece and a means for opening the valve in response to a measured threshold of airflow;

drawing air from the mouthpiece until a threshold is reached so as to cause the valve to open and release a controlled amount of insulin and propellant which is drawn into the lungs of the patient, wherein the device includes a microprocessor connected to the means for measuring airflow and means for opening the valve, the microprocessor being programmed to control the amount of insulin released, based on the needs of the patient, wherein the threshold level is a level calculated to obtain maximum reproducibility in the amount of insulin delivered to the patient with each release of insulin.

* * * * *